United States Patent [19]

Dotta

[11] 4,418,822
[45] Dec. 6, 1983

[54] SEALED PACKAGE FOR WOUND DRESSING ADHESIVE TAPE

[76] Inventor: Angelo Dotta, Via Altabella 10, Bologna, Italy

[21] Appl. No.: 384,531

[22] Filed: Jun. 3, 1982

[30] Foreign Application Priority Data

Jun. 11, 1981 [IT] Italy ............................. 67812 A/81

[51] Int. Cl.³ .......................................... A61F 13/02
[52] U.S. Cl. .................................... 206/441; 128/155
[58] Field of Search ............... 128/155, 156; 206/441, 206/440, 438

[56] References Cited

U.S. PATENT DOCUMENTS 4,235,337 11/1980 Dotta ................................. 128/155

Primary Examiner—Henry J. Recla
Assistant Examiner—Karin M. Reichle
Attorney, Agent, or Firm—Murray Schaffer

[57] ABSTRACT

A rapidly opening sealed package for wound dressing adhesive tape comprising an adhesive support carrying a wound dressing pad covered endwise by a pair of protective films attached to a pair of outer sheaths so that by pulling the outer sheaths apart the protective films will move therewith to separate centrally and uncover the wound dressing pad. An adhesive layer is applied adjacent said wound dressing pad between said protective films and said outer sheaths. In this manner a material of poor adhesive power such as siliconated paper may be used for the protective films.

4 Claims, 3 Drawing Figures

SEALED PACKAGE FOR WOUND DRESSING ADHESIVE TAPE

BACKGROUND OF THE INVENTION

This invention relates to a rapidly opening sealed package for wound dressing adhesive tape, in which materials treated by antiadhesive substances such as siliconated paper or the like, which are normally discarded during the manufacturing process, can be used to make protective films for the wound dressing adhesive tape.

Conventionally wound dressing adhesive tapes are usually made from rolls of plastic film adhesively connected to siliconated paper. During production of the tapes these composite film and paper bands are normally unwound from the roll and perforated and then the siliconated paper is separated from the film covered with adhesive. As the film moves on, a wound dressing pad is attached thereto together with a pair of new protective films which meet and are superimposed on the wound dressing pad where they may also be folded back. Such a wound dressing adhesive tape package is disclosed in U.S. Pat. No. 4,235,337. The siliconated paper is normally discarded as it would not afford an appropriate and attractive covering with folds on the wound dressing pad as the paper is perforated and of the same size as the film covered with adhesive. When using such paper for covering a wound dressing pad, when the latter is removed from its package, it would exhibit two exposed visible surfaces one of which, that of the wound dressing pad, would have a regular well centered perforation whereas the other, that of the protective paper, would be perforated at alternate intervals in positions not coinciding with those of the perforation of the wound dressing pad and the wound dressing pad to be applied to the wound would only be imperfectly covered because of the insufficient size of the surface of the paper and because of its perforation.

Even in the rapidly opening package disclosed in the aforementioned U.S. patent, which partly conceals the drawbacks set out above, it is not possible to use siliconated paper as the latter, if it were folded back outwardly for a short length over the wound dressing pad, would have its folded inner surface facing the wrapping sheet and would be difficult to secure in position because of the antiadhesive treatment. The application of a coating would be difficult and unadvisable because of the cost involved.

It is therefore an object of the present invention to provide a wound dressing adhesive tape package which combines with the high quality of the aforementioned wound dressing package, particularly with regard to the rapidly opening feature, the possibility of using wound dressing pads provided with protective films treated with antiadhesive substances without need of coating or folding and particularly permits to use as the material for the protective films the siliconated paper or plastic material which hitherto was discarded during the manufacturing process and is derived from a supply band on which it is adhesively connected to the plastic film.

SUMMARY OF THE INVENTION

This and other objects, which will become apparent from the following description, are achieved according to the invention by a rapidly opening sealed package for wound dressing adhesive tape, comprising an adhesive support having a nonadhesive wound dressing area carrying a wound dressing pad, a pair of protective films attached to said adhesive support, and an outer wrapper formed substantially of a pair of flat tubular outer sheaths closed at their peripheral edges and having adjacent ends adhesively sealingly connected to one another but separable by pulling them apart, characterized in that said pair of protective films have a small degree of adhesion only at their inner surfaces attached to said adhesive support and each of them is adhesively connected to a separable portion of said wrapper by means of an adhesive layer provided between a portion of an outer surface of each protective film and a corresponding adjacent portion of an inner surface of said wrapper in an area in the vicinity of said wound dressing pad, the overall assembly being of a generally flat configuration and such that when pulling apart said tubular sheaths of said wrapper said protective films will remain adherent in the portion thereof adhesively connected to the corresponding separated portions of said wrapper and will be folded back upon themselves in opposed S and Z shapes and will be detached from said wound dressing pad by sliding within said wrapper formed of said pair of tubular sheaths, exposing said wound dressing pad ready for application.

Thus, the technical problem outlined above has been solved according to the invention by an arrangement based on the poor adhesion of the inner surface of the siliconated paper which permits detachment from the wound dressing pad with a much smaller effort than hitherto was necessary for detaching the conventional protective films. In fact, when the wound dressing pad is arranged in a wrapper which can be separated by pulling it apart, it is possible to keep the protective films of siliconated paper well adhering to the corresponding portions of the wrapper provided that the former are connected to the latter—preferably at the level of the wound dressing pad—by an adhesive of greater adhesive power than the force of adhesion between the wound dressing pad and the siliconated paper surface.

The adhesive must be applied to the non-siliconated outer surface of the protective paper and the corresponding inner surface of the wrapper. When the wrapper is pulled apart, the two siliconated paper portions protecting the wound dressing pad are folded back forming an S and a Z in opposed directions and very flat and are gradually detached from the wound dressing pad which is uncovered and ready for use, remaining substantially flat.

In addition to the great advantage of rapid and almost automatic opening of the wound dressing package without any need of manipulation, the package thus obtained affords the possibility of using protective paper or plastic which is treated with antiadhesive substances and is normally discarded. There is no unpleasant aspect for the user, either, as in the wound dressing package thus produced the perforation of the protective paper is visible only for a short time and length during opening of the package and the delicate covering of the wound dressing pad is completely concealed. It is to be noted that the effect of little conspicuousness of the protective paper films is promoted by their folding in S and Z form during opening of the package. This effect can be enhanced by setting the point of adhesive connection as far as possible toward the edges of the wound dressing pad.

DESCRIPTION OF PREFERRED EMBODIMENT

Figure 1:
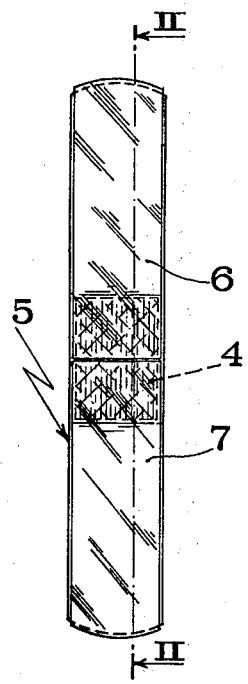
FIG. 1 is a top plan view of a wound dressing adhesive tape package according to the invention without the wrapper.
Figure 2:
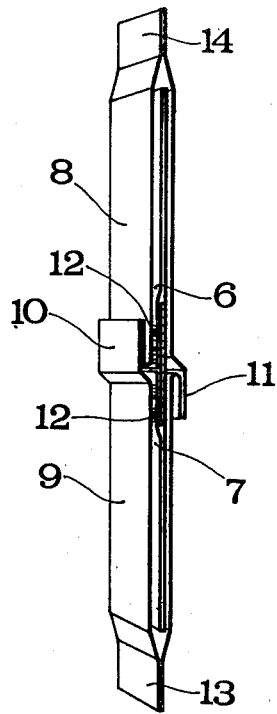
FIG. 2 is a perspective view of the wound dressing adhesive tape package with wrapper and in the closed position and in a longitudinal section taken along the line II—II of FIG. 1.

Referring to FIG. 1, an adhesive support 5 carrying a wound dressing pad 4 is covered by a pair of protective films 6 and 7 the ends of which in the illustrated preferred embodiment are located in the middle of the adhesive support above the wound dressing pad 4. In the illustrated embodiment the protective films are made of transparent material and therefore hardly visible in FIG. 1; however, it is evident from FIG. 1 that these protective films are substantially flat, i.e. they are not folded outwardly. FIG. 2 shows the complete wound dressing adhesive tape package in the closed position. This package substantially comprises a pair of flat tubular outer sheaths 8 and 9 provided with outwardly folded laps 10 and 11 above and below the transverse center line of the wound dressing pad 4. The inner surfaces of the laps 10 and 11 of outer sheaths 8 and 9 are coated with self-sealing substances which when heated permit the outer sheaths to be connected and retained together.

The inner surface of each outer sheath 8 and 9 is connected to the outer surface, i.e. the surface directed away from adhesive support 5, of the protective film 6 or 7, respectively, by a thin layer of adhesive 12 which connects the outer sheaths much more firmly to the protective films than the latter are connected to the adhesive support because the protective films have a siliconated surface facing the adhesive support 5 and having only slight adhesive power.

To avoid irregular folding of the outer sheaths, the adhesive layer 12 is preferably made to extend substantially in a straight line perpendicularly to the sides of wound dressing pad 4.

Also the adhesive layers 12 should preferably extend parallel to each other. Further, in the area of connection of the protective paper films where there is greater stress, the wrapper formed of outer sheaths 8 and 9 is preferably of the same size as the wound dressing pad 4 and such as to be not easily deformable. This is obtained by applying the adhesive to the inner surfaces of the wrapper in two parallel areas or strips adjacent the transverse center separating line between the pair of sheaths forming the wrapper and over the entire width thereof. In this manner also the two inner surfaces of the wrapper extending beyond the sides of the wound dressing pad are covered with adhesive and firmly secured together.

Figure 3:
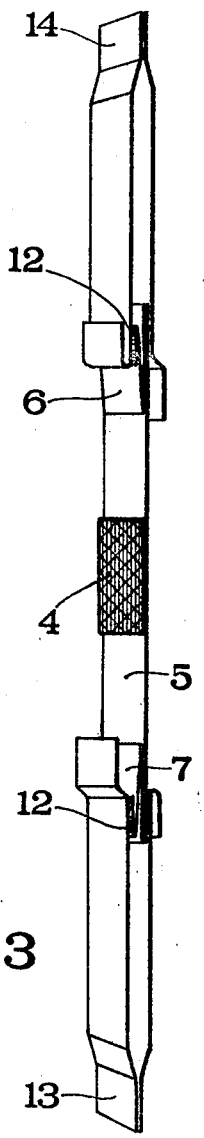
FIG. 3 is a perspective view as in FIG. 2, showing the package as it is being opened.

FIG. 3 shows how the package according to the invention is opened. To open the package it is sufficient to grip the outer ends 13 and 14 of outer sheaths 8 and 9 and pull them apart. Under the effect of the pulling force the two sheaths 8 and 9 are separated in the area of the laps 10 and 11. As the sheaths 8 and 9 move away from each other, they pull the protective films 6 and 7 along with them as the latter adhere more firmly to the sheaths due to the provision of the adhesive layer 12. Regular detachment of the protective films 6 and 7 from the adhesive support 5 is ensured by the fact that the films form an extremely flat Z and S, respectively, during the separating operation during which a portion of the outer surface of each film remains firmly attached to the adjacent inner surface of the outer sheath 8 and 9, respectively, through the adhesive layer 12.

The described wound dressing adhesive tape package permits the adhesive support 5 and the wound dressing pad 4 to be rapidly uncovered, as desired, without having to touch the wound dressing pad or the adhesive support.

The width of the complete outer wrapper is not shown in the drawings as this is within the scope of the prior art. However, conveniently the width of the outer wrapper is made slightly greater than that of the adhesive support 5 so that both the projecting ends 13 and 14 and the sides of the wrapper can be sealed around the wound dressing pad 4 in a pocket of appropriate size.

Although a preferred embodiment of the invention has thus been described in detail and illustrated in the accompanying drawings, it is to be understood that the invention is not limited to this precise embodiment and that numerous changes and modifications obvious to one skilled in the art, particularly with regard to the size and relative dimensions of the parts of the described wound dressing adhesive tape package, may be made therein without departing from the scope of the invention as defined by the appended claims.

I claim:

1. A rapidly opening sealed package for wound dressing adhesive tape, comprising an adhesive support having a non-adhesive wound dressing area carrying a wound dressing pad, a pair of protective films attached to said adhesive support, and an outer wrapper formed substantially of a pair of flat tubular outer sheaths closed at their peripheral edges and having adjacent ends adhesively sealingly connected to one another but separable by pulling them apart, characterized in that said pair of protective films have a small degree of adhesion only at their inner surfaces attached to said adhesive support, and each of them is adhesively connected to a separable portion of said wrapper by means of an adhesive layer provided between a portion of an outer surface of each protective film and a corresponding adjacent portion of an inner surface of said wrapper in an area in the vicinity of said wound dressing pad, the overall assembly being of a generally flat configuration and such that when pulling apart said tubular sheaths of said wrapper said protective sheaths will remain adherent in the portion thereof adhesively connected to the corresponding separated portions of said wrapper and will be folded back upon themselves in opposed S and Z shapes and will be detached from said wound dressing pad by sliding within said wrapper formed of said pair of tubular sheaths, exposing said wound dressing pad ready for application.

2. A rapidly opening sealed package for wound dressing adhesive tape as claimed in claim 1, wherein said protective films are made of siliconated paper.

3. A rapidly opening sealed package for wound dressing adhesive tape as claimed in claim 1, wherein said protective films are made of siliconated plastic material.

4. A rapidly opening sealed package for wound dressing adhesive tape as claimed in claim 1, wherein said adhesive layer for securing said protective films to said outer sheaths is previously applied to the inner surface thereof in two substantially parallel areas laterally of the center separating line therebetween and perpendicularly thereto over a width corresponding to that of said outer sheaths.

* * * * *